United States Patent [19]

Gloor

[11] 4,357,159
[45] Nov. 2, 1982

[54] HALOETHYLTHIENYLSULPHONATES FOR THE REGULATION OF PLANT METABOLISM

[75] Inventor: Bernhard Gloor, Muttenz, Switzerland

[73] Assignee: Ciba-Geigy Corporation, Ardsley, N.Y.

[21] Appl. No.: 8,623

[22] Filed: Feb. 1, 1979

Related U.S. Application Data

[62] Division of Ser. No. 867,652, Jan. 6, 1978, Pat. No. 4,149,873.

[51] Int. Cl.$^3$ .............................................. A01N 43/10
[52] U.S. Cl. .......................................... 71/90; 71/73; 549/66
[58] Field of Search ................ 71/103, 73, 90; 549/66

[56]  References Cited

U.S. PATENT DOCUMENTS

| | | | |
|---|---|---|---|
| 3,275,506 | 9/1966 | Szabo et al. | 424/303 |
| 3,701,776 | 10/1972 | Pillon et al. | 549/66 X |
| 3,885,951 | 5/1975 | Hofer et al. | 71/103 |
| 3,887,354 | 6/1975 | Archer | 71/90 |
| 3,941,826 | 3/1976 | Martin | 71/103 X |
| 3,966,961 | 6/1976 | Varsanyi et al. | 424/303 |
| 3,978,228 | 8/1976 | Yoshinaga et al. | 71/103 X |
| 4,009,190 | 2/1977 | Baker | 71/103 X |

FOREIGN PATENT DOCUMENTS

| | | |
|---|---|---|
| 2141586 | 3/1972 | Fed. Rep. of Germany . |
| 2163192 | 7/1972 | Fed. Rep. of Germany . |
| 1534046 | 6/1968 | France . |
| 497299 | 4/1974 | U.S.S.R. . |

*Primary Examiner*—Catherine L. Mills
*Attorney, Agent, or Firm*—Frederick H. Rabin; Harry Falber

[57]  ABSTRACT

A composition and a method for regulating the plant-metabolism, especially for promoting the abcission of citrus fruit and olives are disclosed, which use as active component a sulphonyl ester of the formula

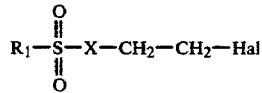

wherein
 $R_1$ is an alkyl, alkenyl, phenyl naphthyl, diphenyl or thienyl radical,
 X is oxygen or sulphur and
 Hal is a halogen atom.

6 Claims, No Drawings

HALOETHYLTHIENYLSULPHONATES FOR THE REGULATION OF PLANT METABOLISM

This divisional of application Ser. No. 867,652 filed on Jan. 6, 1978 now U.S. Pat. No. 4,149,873.

The present invention provides a composition for the regulation of plant metabolism, in particular for promoting fruit abscission, which contains sulphonic acid esters as active ingredient, as well as a method of promoting the abscission of fruit.

These esters promote in particular the ripening and abscission of fruit and are suitable active compounds for facilitating harvesting, chiefly in the cultivation of olives and citrus fruit.

The sulphonic acid esters have the formula I

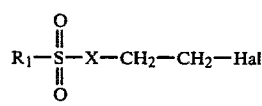

wherein
$R_1$ is a $C_1$-$C_8$alkyl radical which is unsubstituted or mono- or polysubstituted by halogen, cyano, by a substituted or unsubstituted phenyl or benzoyl radical, a $C_2$-$C_8$alkenyl radical which is unsubstituted or mono- or polysubstituted by halogen, or is a phenyl, naphthyl, diphenyl or thienyl radical which can be substituted or unsubstituted,
X is an oxygen or sulphur atom and
Hal is a fluorine, chlorine, bromine or iodine atom.

The phenyl, naphthyl or diphenyl radical or a phenyl or benzoyl radical attached to an alkyl radical can be unsubstituted or mono- or polysubstituted by halogen atoms, especially chlorine, bromine or iodine, by the nitro or trifluoromethyl group, $C_1$-$C_4$alkyl radicals, an alkanoic acid amide group, the alkane group of which contains 1 to 4 carbon atoms, or by an alkoxy, alkylthio, alkylsulphinyl or alkylsulphonyl group which contains 1 to 4 carbon atoms in the alkyl moiety. The thienyl radical can be unsubstituted or mono- to tri-substituted by halogen atoms, especially chlorine, bromine or iodine atoms, the trifluoromethyl group or a lower alkyl radical of 1 to 4 carbon atoms.

The compounds of the formula I are partly liquid and partly solid compounds. They speed up the ripening and abscission of fruit of all kinds and are used in particular for facilitating the harvesting of olives and citrus fruit. Since these compounds are only slightly phytotoxic or not phytotoxic at all, their application damages neither fruit, trees, leaves, nor—in the case of citrus fruit—any blossoms still present on the trees. These compounds can also be used for stimulating the flow of resin, this is important where resin is industrially utilised, for example the latex of rubber trees or the resins of certain conifers for obtaining terpentine oil.

Furthermore, the application of the compounds of the formula I speeds up the ripening of fruit on plants or also of harvested plants. This action can be of importance in the cultivation and ripening of tomatoes and peppers to satisfy market requirements.

Particularly active compounds are the 2-iodoethyl esters of the sulphonic acids of the formula II

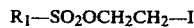

wherein $R_1$ is as defined in formula I, and the 2-bromoethyl esters of thienylsulphonic acids of the formula III

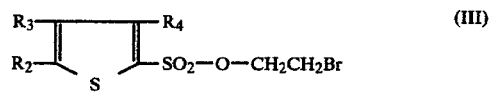

wherein $R_2$, $R_3$ and $R_4$ represent hydrogen, $C_1$-$C_4$alkyl, chlorine, bromine, iodine or trifluoromethyl.

Compounds having good action are also the 2-halogenoethylthiosulphonates of the formula IV

wherein $R_1$ and Hal are as defined in formula I and Hal' represents chlorine or bromine.

The sulphonic acid esters of the formula I can be prepared by different methods of synthesis which are known per se.

In a first process, an acid halide, a fluoride, chloride or bromide of the formula V is reacted with 2-halogenoethanol of the formula VI, optionally in the presence of an acid acceptor:

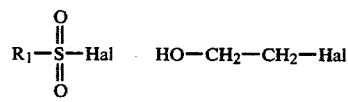

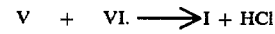

In the above formulae, $R_1$ is as defined in formula I and Hal represents a halogen atom, preferably a chlorine, bromine or iodine atom.

Such a process has been described for example by R. K. Crossland and K. L. Servis in J. Org. Chem. 35, 3195 (1970) or by W. C. J. Ross and W. Davis in J. Chem. Soc. 1957, 2420.

The esters of the formula I can be prepared in an entirely similar manner by reacting a sulphonic acid of the formula VII with thionyl chloride and the 2-halogenoethanol of the formula VI:

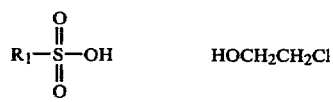

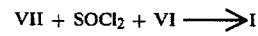

In the above formulae, $R_1$ and Hal are as defined in formula I.

This process has been described for example by A. Etienne et al. in Cont. Rend. Acad. Sci. Paris C 275, 633 (1972) or in French Pat. No. 1,475,830.

This esterification is performed in a very simple manner by reacting the silver salt of a sulphonic acid of the formula VII direct with a 1,2-dihalogenoethane of the formula VIII according to the reaction scheme:

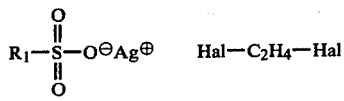

VII + VIII ⟶ I + AgHal.

wherein $R_1$ and Hal are as defined in formula I.

This process has been suggested by W. D. Emmons and A. F. Ferris in J. Am. Chem. Soc. 75, 2257 (1953).

The thiosulphonates of the formulae I and IV can also be prepared by reacting an alkali metal salt, for example the sodium or potassium salt, of a thiosulphonic acid of the formula XI with a reactive derivative of a 2-halogenoethanol of the formula X:

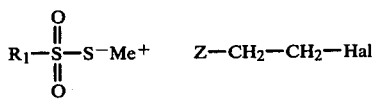

IX + X ⟶ I + MeZ wherein $R_1$ and Hal are as defined in formula I, Me is an alkali metal and Z is a nucleophilic leaving group. A process of this kind is described for example in U.S. Pat. No. 3,275,506.

The thiosulphonates of the formula I and IV can also be obtained by reacting a sulphinic acid of the formula XI or one of the alkali metal salts thereof, with a sulphenyl halide of the formula XII, optionally in the presence of an acid acceptor:

$$R_1-SO_2^-Me^+ \quad Y-S-CH_2CH_2-Hal$$

XI + XII ⟶ I + MeY wherein $R_1$ and Hal are as defined in formula I, Me is hydrogen or an alkali metal and Y is fluorine, chlorine or bromine.

Finally, the thiosulphonates of the formula I and IV can be obtained by reacting a sulphinic acid of the formula XIII with a mercaptan of the formula XVI in the presence of an alkyl nitrite, for example ethyl nitrile:

$$R_1-SO_2H + HS-CH_2-CH_2Hal$$

XIII + XIV ⟶ I

This process has been described for example by B. G. Boldyrev in Zh. Organ. Khim. 2, 286 (1966), CA 65, 2162 c.

The following Examples illustrate the preparation of a number of arbitrarily chosen sulphonates and thiosulphonates of the formula I. Further esters, which have been synthesised in analogous manner, are listed in the following tables.

EXAMPLE 1

2-Iodoethylmethanesulphonate (compound 1)

To 51.5 g of iodoethanol (0.3 mole) in 200 ml of dry ethanolfree chloroform were added 50.5 g of triethylamine (0.5 mole) at 0° C. and the resulting solution was cooled to −30° C. At this temperature, 36.6 g of methanesulphonyl chloride (0.32 mole) were slowly added dropwise with stirring. Stirring was then continued until the solution reached room temperature. After extraction with dilute hydrochloric acid and neutralisation with bicarbonate solution, the chloroform solution was washed with saline solution and then dried over sodium sulphate. The solvent was then stripped off at 30° C. and 15 torr. The residual oil (72 g, 96% yield) was identified by NMR spectography as pure 2-iodoethylmethanesulphonate. (Absorption in CDCl$_3$, chemical displacement based on TMS in ppm [δ]:S, 3, 10, 3H; T, 3, 40, 2H, I=7 Hz; T, %, 49, 2H, I=7 Hz).

EXAMPLE 2

2-Iodoethyl-2,4-dimethylbenzenesulphonate (compound 26)

15.4 g of 2,4-dimethylbenzenesulphochloride (75 mmols) were dissolved in 30 ml of methylene chloride and to the solution were added 15.5 g (90 mmols) of iodoethanol. To this solution were slowly added dropwise 11.9 g of pyridine (150 mmols) dissolved in 15 ml of methylene chloride, while keeping the reaction temperature between −5° and +5° C. The solution was stirred for 12 hours at the same temperature, then washed with water, 1% hydrochloric acid and saline solution. The organic phase was dried over sodium sulphate and concentrated, affording 21.8 g of an oil (91.6% of theory); $n_D^{20}$: 1.5706.

Analysis:

calculated: 35.31% C, 3.81% H, 9.43% S 37.31% I; found: 35.8% C, 3.9% H, 9.6% S 37,2% I.

EXAMPLE 3

2-Chloroethyl-methanethiosulphonate (compound 19)

300.5 g (2 moles) of potassium methanethiosulphonate were stirred together with 435 g of 1-bromo-2-chloroethane (3.03 moles) in 450 ml of isobutanol for 5 hours at 90° to 100° C., then for 16 hours at room temperature. Precipitated salt was then filtered off, the filtrate concentrated in vacuo and the resulting oil taken up in 300 ml of ether. The ethereal solution was washed with water and saline solution, then dried over sodium sulphate. The ether was evaporated off, affording 290 g of an oil which was distilled over a 10 cm Vigreux column under a pressure of 0.05 torr and at a temperature between 95° and 100° C. Yield: 231 g (63% of theory) of product.

Elemental analysis:

calculated: 20.63% C, 4.04% H, 36.71% S, 20.30% Cl; found: 21.1% C, 4.1% H, 36% S, 20.5% Cl.

The following compounds were prepared by methods analogous to those described in the foregoing Examples.

| No. | Structure | Physical constant (°C.) |
|---|---|---|
| 1 | CH$_3$—SO$_2$—O—CH$_2$—CH$_2$—I | b.p.: 140°/6 torr |
| 2 | CH$_3$CH$_3$—SO$_2$—O—CH$_2$—CH$_2$—I | $n_D^{20}$ 1.513 |
| 3 | CH$_3$CH$_2$CH$_2$—SO$_2$—O—CH$_2$CH$_2$—I | $n_D^{20}$ 1.44 |

-continued

| No. | Structure | Physical constant (°C.) |
|---|---|---|
| 4 | (CH₃)₂CH—SO₂—O—CH₂CH₂—I | $n_D^{25}$ 1.5098 |
| 5 | CH₃CH₂CH₂CH₂—SO₂—OCH₂CH₂—I | $n_D^{20}$ 1.520 |
| 6 | Cl—CH₂CH₂CH₂—SO₂—O—CH₂CH₂—I | $n_D^{20}$ 1.527 |
| 7 | C₆H₅—SO₂—O—CH₂CH₂—I | $n_D^{20}$ 1.5762 |
| 8 | CH₃—C₆H₄—SO₂—O—CH₂CH₂—I | $n_D^{20}$ 1.5696 |
| 9 | 2-NO₂-C₆H₄—SO₂—O—CH₂CH₂—I | $n_D^{20}$ 1.558 |
| 10 | CH₃O—C₆H₄—SO₂—O—CH₂CH₂—I | oil |
| 11 | 2,4,5-Cl₃-C₆H₂—SO₂—O—CH₂CH₂—I | m.p. 96–97° |
| 12 | CH₃CO—NH—C₆H₄—SO₂—OCH₂CH₂—I | m.p. 125–27° |
| 13 | 2-Naphthyl—SO₂OCH₂CH₂—I | m.p. 70–71° |
| 14 | 2-Thienyl—SO₂—OCH₂CH₂—I | oil |
| 15 | 2-Thienyl—SO₂—OCH₂CH₂—Cl | b.p.: 118°/0.04 torr |
| 16 | 2-Thienyl—SO₂—O—CH₂CH₂—Br | b.p.: 142–44°/0.04 torr |
| 17 | 5-Cl-2-Thienyl—SO₂—O—CH₂CH₂—Br | $n_D^{20}$ 1.5635 |
| 18 | 5-Br-2-Thienyl—SO₂—O—CH₂CH₂—Br | $n_D^{20}$ 1.5825 |
| 19 | CH₃—SO₂—S—CH₂CH₂—Cl | b.p.: 80°/0.01 torr |
| 20 | CH₃—C₆H₄—SO₂—S—CH₂CH₂—Cl | $n_D^{24}$ 1.5788 |
| 21 | 2-Thienyl—SO₂—S—CH₂CH₂—Cl | $n_D^{20}$ 1.623 |
| 22 | CH₃(CH₂)₃—SO₂—S—CH₂CH₂—Cl | $n_D^{20}$ 1.5123 |
| 23 | CH₃—SO₂—S—CH₂CH₂—Br | b.p.: 96–106°/0.03 torr |

-continued

| No. | Structure | Physical constant (°C.) |
|---|---|---|
| 24 | CH₃—⟨phenyl⟩—SO₂—S—CH₂CH₂—Br | $n_D^{20}$ 1.6010 |
| 25 | 2,5-dimethylphenyl—SO₂—O—CH₂CH₂—I | $n_D^{20}$ 1.5645 |
| 26 | 2,4-dimethylphenyl—SO₂—O—CH₂CH₂—I | $n_D^{20}$ 1.5706 |
| 27 | 2-naphthyl—SO₂—O—CH₂CH₂—Br | m.p. 38° |
| 28 | CH₃—SO₂—O—CH(C₃H₇-n)—CH₂—Br | oil |
| 29 | Cl—CH₂CH₂CH₂—SO₂—O—CH₂CH₂Br | oil |
| 30 | 1-naphthyl—SO₂—O—CH₂CH₂—Br | oil |
| 31 | BrCH₂CH₂SO₂—O—CH₂CH₂Br | b.p.: 104–9°/0.04 torr |
| 32 | CH₃O—⟨phenyl⟩—SO₂OCH₂CH₂Br | oil |
| 33 | CH₃CONH—⟨phenyl⟩—SO₂OCH₂CH₂—Br | m.p.: 122–4° |
| 34 | 2,4,5-trichlorophenyl—SO₂O—CH₂CH₂—Br | m.p.: 109–11° |
| 35 | 2-nitrophenyl—SO₂O—CH₂CH₂—Br | oil |
| 36 | 2-methyl-thienyl—SO₂OCH₂CH₂—Br | $n_D^{20}$ 1.5501 |
| 37 | Cl—CH₂—SO₂OCH₂CH₂—I | |
| 38 | phenyl—CH₂SO₂OCH₂CH₂—I | m.p. 52–4° |
| 39 | phenyl—CH₂CH₂CH₂SO₂OCH₂CH₂—I | |
| 40 | 3-methyl-thienyl—SO₂OCH₂CH₂—I | oil |
| 41 | 5-chloro-thienyl—SO₂OCH₂CH₂—I | |

| No. | Structure | Physical constant (°C.) |
|-----|-----------|--------------------------|
| 42  | Br—⟨S⟩—SO₂—OCH₂CH₂—I | |
| 43  | Cl—⟨S⟩(Cl)—SO₂OCH₂CH₂—I | |
| 44  | Br—⟨S⟩(Br)—SO₂—OCH₂CH₂—I | |
| 45  | CH₃—CH(CN)—SO₂OCH₂CH₂—I | |
| 46  | CH₃—CH(CN)—SO₂OCH₂CH₂—Cl | |
| 47  | CH₃SO₂—S—CH₂CH₂—I | |
| 48  | CH₃—⟨C₆H₄⟩—SO₂—S—CH₂—CH₂—I | |
| 49  | ⟨S⟩—SO₂—S—CH₂—CH₂—I | |
| 50  | ⟨C₆H₅⟩—CO—CH₂SO₂OCH₂CH₂—I | |
| 51  | Cl—⟨C₆H₁₀⟩—CO—CH₂SO₂OCH₂CH₂—Br | |
| 52  | Cl—⟨C₆H₄⟩—CH₂SO₂SCH₂CH₂—Cl | |
| 53  | CH₃—⟨C₆H₄⟩—CH₂SO₂OCH₂CH₂—I | |
| 54  | CH₃—⟨C₆H₁₀⟩—CO—CH₂SO₂OCH₂CH₂Cl | |
| 55  | CH₃—CH(CN)—SO₂OCH₂CH₂—Br | |
| 56  | Cl—CH₂CH₂SO₂OCH₂CH₂Cl | |
| 57  | ⟨naphthyl⟩—SO₂OCH₂CH₂Cl | |
| 58  | ⟨C₆H₄(CF₃)⟩—SO₂OCH₂CH₂Cl | |
| 59  | ⟨naphthyl-CH₃⟩—SO₂OCH₂CH₂—I | |

-continued

| No. | Structure | Physical constant (°C.) |
|---|---|---|
| 60 | naphthalene with CH₃ and SO₂OCH₂CH₂—I | |
| 61 | naphthalene with SO₂OCH₂CH₂—I, CH₃, CH₃ | |
| 62 | biphenyl—SO₂OCH₂—CH₂—I | |
| 63 | phenyl(CF₃)—SO₂OCH₂CH₂—I | |
| 64 | CH₃CONH—phenyl(CF₃)—SO₂OCH₂CH—I | |
| 65 | CF₃—phenyl(NH—COCl)—SO₂OCH₂CH₂—I | |
| 66 | Br—phenyl—SO₂OCH₂CH₂—I | |
| 67 | phenyl(Cl)(CF₃)—SO₂OCH₂CH₂—I | |
| 68 | Cl—phenyl(CF₃)(Cl)—SO₂OCH₂CH₂—I | |

The compounds of the formula I are able to regulate the plant metabolism. They promote in particular the ripening of fruit and the formation of separation tissue, especially between fruit and stem. Fruit of all kinds, for example stone fruit (olives) and citrus fruit, such as oranges, lemons, grapefruit etc., can thereby be detached from the stems manually or mechanically without exerting great force. The damage normally caused to the leaves and branches of the plant when the trees and branches are shaken during harvesting and when the fruit is plucked off is to a large extent avoided and the productivity of the trees is accordingly increased.

The extent and nature of the action depend on the most widely differing factors which vary according to the species of plant, in particular on the application concentration, the time of application with regard to the development stage of the plant and the fruit. Accordingly, for example, plants whose fruit is used or processed are treated directly after flowering or in the corresponding interval of time from harvesting. Application is made preferably in the form of liquid compositions both to the parts of plants above the soil and into and onto the soil. The preferred mode of application is to the parts of plants above the soil, for which purposes solutions or aqueous dispersions are most suitable.

The active substances (compounds) of the formula I are used together with suitable carriers and/or other additives. Suitable carriers and additives can be solid or liquid and correspond to the substances conventionally used in the art of formulation, for example natural or regenerated mineral substances, solvents, dispersants, wetting agents, tackifiers, thickening agents or binders.

The rates of application depend substantially on the end-use application and on the nature of the application (treatment of soil or parts of plant). The conventional rates of application for soil treatment and in areas of arable land are between 0.1 and 10 kg of active substance per hectare of plant crop, preferably 0.4 to 4 kg of active substance per hectare.

The compositions for promoting abscission and advancing ripening which contain active compounds of the formula I can be formulated as non-aqueous solutions, dispersions, emulsifiable concentrates, wettable powders or as dusts, to which antioxidants, for example hydroquinone, can be added. Such formulations can contain 2 to 95% by weight of active substance and can be prepared by the techniques conventionally employed in agricultural chemistry. Aqueous preparations having a content of 0.01 to 1% of a non-ionic wetting agent are preferred.

The time of application for the abscission of fruit is shortly before harvesting, i.e. 3 days to 4 weeks before harvesting, and for the advancement of ripening shortly before or after the picking of fruit.

When the compositions of the present invention are used as ripening promoters, uniform ripening occurs without detriment to the quality of the fruit.

Both the treatment before and after picking is effected by sprinkling, spraying or dusting, and after harvesting also by immersing the fruit in a liquid active substance formulation. Pretreatment 7 to 10 days before the intended harvesting is preferred.

For ripening, rates of application of 0.5 to 1 kg of active substance per hectare suffice. The non-phytotoxicity of the majority of the active substances is a substantial advantage of the ripening promoters of the present invention.

The following methods were employed to determine the abscission action on citrus plants: Parts of branches of orange trees (Hamlin, Pineapple and Valencia varieties) bearing at least 20 fruit were sprinkled with active substance solutions shortly before harvesting. Evaluation was made after 7 days, using two different systems:

(a) measurement of the plucking force and its percentage decrease in relation to the untreated control (=100%);

(b) the number of fruit that have fallen without shaking expressed in %, compared with untreated control (=0%).

While causing no or only slight leaf drop, the tested compounds effected a pronounced formation of separation tissue on the fruit stems, a marked reduction in the plucking force, and many even had good fruit drop values.

The following values were measured: Percentage reduction in the plucking force 8 days after treatment in comparison with that of untreated fruit, amounting to 9 to 11 kg per orange.

| Variety of orange | Navel (Spain) | Salustiana (Spain) | Valencia (USA) |
|---|---|---|---|
| compound 1 | | | |
| 4000 ppm | 75% | 75% | 68% |
| 2000 ppm | 37% | 80% | 5% |
| 1000 ppm | 28% | 31% | 6% |
| compound 8 | | | |
| 1000 ppm | 93% | | |
| 500 ppm | 68% | | |
| 250 ppm | 60% | | |

Similar experiments were carried out on olive trees. Parts of branches were sprayed with a strongly diluted active substance solution 8 days before the expected time of harvesting, while simultaneously counting the number of olives on the respective part of the branch. Similarly large parts of branches on the same tree were left untreated as control. After 8 days the branches were uniformly shaken by hand and the number of fallen olives determined in %. These experiments were carried out on olive trees of different varieties in Italy, Spain and the U.S.A.

| | % age fruit drop 8 days after treatment | | | | |
|---|---|---|---|---|---|
| Variety of olive | Coratina (Italy) early harvest | Coratina (Italy) late harvest | Ogliera (Italy) | Zorzaleno (Spain) | Hojiblanca (Spain) |
| Compound 8 | | | | | |
| 1500 ppm | 97% | 100% | 88% | 91% | 98% |
| 750 ppm | 94% | 96% | 83% | 81% | 98% |
| 375 ppm | 86% | 81% | 52% | 67% | 94% |
| untreated control | 37% | 24% | 13% | 36% | 62% |
| Variety of olive | Picual (Spain) | Dritta di Pianella (Italy) | Moraiolo (Italy) | Manzanillo (USA) | Mission (USA) |
| Compound 8 | | | | | |
| 1500 ppm | 92% | 100% | 75% | 79% | 98% |
| 750 ppm | 89% | 84% | 65% | 70% | 98% |
| 375 ppm | 93% | 91% | 30% | 26% | 77% |
| untreated control | 63% | 16% | 20% | 8% | 3% |

In these test, the leaf fall was always less than 5%.

The compositions of the present invention are prepared in known manner by intimately mixing and/or grinding active substances of the formula I with suitable carriers, with or without the addition of dispersants or solvents which are inert to the active substances. The active substances may be formulated as follows:

| water-dispersible active substance concentrates: | wettable powders, emulsifiable concentrates |
|---|---|
| liquid formulations: | solutions. |

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances nd anti-foam agents and, if appropriate, solvents. The active substance concentration in these compositions is 5 to 80%.

Wettable powders are obtained by mixing and grinding the active substances with dispersing agents and powdered carriers in suitable devices until homogeneity is attained. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

As dispersing agents there can be used, for example, condensation products of sulphonated naphthalene and sulphonated naphthalene derivatives with formaldehyde, condensation products of naphthalene or naphthalenesulphonic acids with phenol and formaldehyde, as well as alkali metal, ammonium and alkaline earth metal salts of ligninsulphonic acid, in addition, alkylaryl sulphonates, alkali metal and alkaline earth metal salts of dibutylnaphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetylene glycols, dialkyldilaurylammonium chloride and fatty acid alkali metal and alkaline earth metal salts.

Suitable anti-foam agents are for example silicones.

The active substances are mixed, ground sieved and strained with the above additives such that, in wettable powders, the particle size of the solid consistant does not exceed 0.02 to 0.04 mm. Emulsfifiable concentrates are prepared by using the dispersing agents referred to above, organic solvents, and water. Examples of suitable solvents are: alcohols, benzene, xylenes, toluene, dimethyl sulphoxide, and mineral oil fractions which boil between 120° and 350° C. The solvents must be practically odourless, not phytotoxic, inert to the active substances and not readily inflammable.

Furthermore, the compositions according to the invention can be applied in the form of solutions. For this purpose the active substances or several active substances of the general formula I are dissolved in suitable organic solvents, mixtures of solvents, or in water. Aliphatic and aromatic hydrocarbons, chlorinated derivatives thereof, alkylnaphthalenes and mineral oils, by themselves or in admixture, can be used as organic solvents. The solutions will contain the active substances in a concentration from 1 to 20%.

The compositions of the present invention can be mixed with other biocidally active substances or agents, for example fungicides, bactericides, fungistats or bacteriostats. They can also contain trace elements etc.

Formulations of the novel active compounds of the formula I are described hereinafter. The parts denote parts by weight.

Wettable powder

The following substances are used to prepare 25% wettable powders:

(a) 25 parts of 2-chloroethyl-methanethiosulphonate
8 parts of a mixture of nonylphenolpolyoxyethylene and calcium dodecylbenzenesulphonate
2 parts of octylphenoxyethylene glycol with 9 to 10 moles of ethylene oxide per mole of octylphenol
5 parts of silicic acid
60 parts of kaolin;
25 parts of active substance
8 parts of a mixture of nonylphenolpolyoxyethylene and calcium dodecylbenzenesulphonate
2 parts of octylphenoxyethylene glycol with 9 to 10 moles of ethylene oxide per mole of octylphenol
10 parts of silicic acid
55 parts of kaolin;
25 parts of active substance
25 parts of silicic acid
5 parts of the condensation product of naphthalenesulphonic acid/phenolsulphonic acid/formaldehyde (3:2:1)
5 parts of sodium dibutylnaphthylsulphonate
40 parts of kaolin;
25 parts of active substance
7.5 parts of silicic acid
5.3 parts of octylphenol octaglycol ether
2.2 parts of sodium 1-benzyl-2-stearyl-benzimidazole-6,3'-disulphonate
0.5 parts of oleic acid
59.5 parts of bolus alba.

The indicated active substance is applied to the corresponding carriers (kaolin and bolus) and then mixed and ground therewith, to give wettable powders of excellent wettability and suspension power. Suspensions of the desired concentration can be obtained from these wettable powders by diluting them with water.

Paste

The following substances are used to prepare a 45% paste:
45 parts of 2-iodoethyl-p-toluenesulphonate
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to prepare suspensions of the desired concentration of active substance.

Emulsifiable concentrate

A 25% emulsifiable concentrate is prepared by mixing the following ingredients:
(a)
   250 g of 2-iodoethyl-$\beta$-naphthalenesulphonate
   10 g of octylphenoxyethyl glycol containing 9 to 10 moles of ethylene oxide per mole of octylphenol
   250 g of methanol made up to
   1000 ml with water
(b)
   250 g of active substance
   100 g of a mixture of alkylarylsulphonate and alkylarylpolyglycol ether made up to
   1000 ml with water
(c)
   250 g of active substance
   100 g of a mixture of alkylarylsulphonate and alkylarylpolyglycol ether made up to
   1000 ml with water
(d)
   250 g of active substance
   100 g of emulsifier (G-3634 A) made up to
   1000 ml with benzyl alcohol;
(e)
   250 g of active substance
   100 g of emulsifier (G-3634 A) made up to
   1000 ml with benzyl alcohol.

This concentrate can be diluted with water to give emulsions of the appropriate concentrations.

Granules

The following substances are used to produce 5% granules:
5 parts of 2-iodoethyl-methanesulphonate
0.25 parts of epichlorohydrin,
0.25 parts of cetyl polyglycol ether,
3.50 parts of polyethyene glycol ("Carbowax"),
91 parts of kaolin (particle size 0.2–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

What is claimed is:

1. A method for promoting the abscission of fruit which comprises applying to a fruit bearing plant or to a fruit itself an effective amount of a compound of the formula $$R_1-SO_2-X-CH_2CH_2-Hal$$

wherein

R$_1$ is thienyl optionally mono- to tri-substituted by one or more members selected from the group consisting of halogen, C$_1$–C$_4$ alkyl and trifluoromethyl, X is oxygen or sulphur, and Hal is fluorine, chlorine, bromine or iodine.

2. A method according to claim 1 which comprises applying to the fruit trees shortly before harvest an effective amount of a compound in which X is oxygen and Hal is iodine.

3. A method according to claim 1 which comprises applying to fruit trees shortly before harvest a compound of the formula

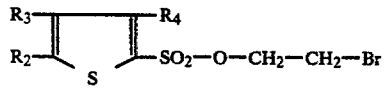

wherein each of R$_2$, R$_3$ and R$_4$ is hydrogen, C$_1$–C$_4$ alkyl, chlorine, bromine, iodine or trifluoromethyl.

4. A method according to claim 1 for promoting the abscission of citrus fruit and olives which comprises applying said compound to citrus or olive trees shortly before harvest.

5. The method according to claim 4 in which the compound is 5-bromo-2-bromoethyl-2-thienylsulphonate.

6. The method according to claim 4 in which the compound is 5-methyl-2-iodoethyl-2-thienylsulphonate.

* * * * *